United States Patent [19]

Semple et al.

[11] Patent Number: 5,576,471
[45] Date of Patent: *Nov. 19, 1996

[54] COBALT-CATALYZED PROCESS FOR PREPARING 1,3-PROPANEDIOL USING A LIPOPHILIC DIHYDROXYARENE PROMOTER

[75] Inventors: Thomas C. Semple, Friendswood; Joseph B. Powell; Lynn H. Slaugh, both of Houston; Thomas C. Forschner, Richmond; Paul R. Weider, Houston, all of Tex.

[73] Assignee: Shell Oil Company, Houston, Tex.

[ * ] Notice: The term of this patent shall not extend beyond the expiration date of Pat. No. 5,463,144.

[21] Appl. No.: 316,669

[22] Filed: Sep. 30, 1994

[51] Int. Cl.$^6$ .................................................. C07C 27/04
[52] U.S. Cl. .......................... 568/862; 568/454; 568/483
[58] Field of Search ..................... 568/483, 454, 568/862

[56] References Cited

U.S. PATENT DOCUMENTS

| | | | |
|---|---|---|---|
| 3,168,553 | 2/1965 | Slaugh | 260/497 |
| 3,456,017 | 7/1969 | Smith | 260/602 |
| 3,463,819 | 8/1969 | Smith | 260/602 |
| 3,687,981 | 8/1972 | Lawrence | 260/340.7 |
| 4,137,240 | 1/1979 | Peterson | 260/340.7 |
| 4,255,279 | 3/1981 | Spohn | 252/413 |
| 4,404,119 | 9/1983 | Lagace | 252/413 |
| 4,873,378 | 10/1989 | Murphy | 568/867 |
| 4,873,379 | 10/1989 | Murphy | 568/867 |
| 4,973,741 | 11/1990 | Beavers | 560/179 |
| 5,030,766 | 7/1991 | Briggs | 568/496 |
| 5,053,562 | 10/1991 | Tau | 568/867 |
| 5,210,318 | 5/1993 | Briggs | 568/496 |
| 5,225,387 | 7/1993 | Briggs | 502/167 |
| 5,256,827 | 10/1993 | Slaugh | 568/454 |
| 5,321,168 | 6/1994 | Roussel | 568/882 |

OTHER PUBLICATIONS

Falbe, Carbon Monoxide In Organic Synthesis, Springer–Verlag (1970), pp. 14–15.
Falbe, New Synthesis With Carbon Monoxide, Springer–Verlag (1980), p. 131.

*Primary Examiner*—Rebecca Cook

[57] ABSTRACT

1,3-Propanediol is prepared in a process which involves reacting ethylene oxide with carbon monoxide and hydrogen in an essentially non-water-miscible solvent in the presence of a non-phosphine-ligated cobalt catalyst and a lipophilic dihydroxyarene promoter to produce an intermediate product mixture containing 3-hydroxypropanal in an amount less than 15 wt %; extracting the 3-hydroxypropanal from the intermediate product mixture into an aqueous liquid at a temperature less than about 100° C. and separating the aqueous phase containing 3-hydroxypropanal from the organic phase containing cobalt catalyst; hydrogenating the 3-hydroxypropanal in the aqueous phase to 1,3-propanediol; and recovering the 1,3-propanediol.

The process enables the production of 1,3-propanediol in high yields and selectivity without the use of a phosphine ligand-modified cobalt catalyst.

16 Claims, 1 Drawing Sheet

COBALT-CATALYZED PROCESS FOR PREPARING 1,3-PROPANEDIOL USING A LIPOPHILIC DIHYDROXYARENE PROMOTER

BACKGROUND OF THE INVENTION

This invention relates to the preparation of 1,3-propanediol. In one aspect, the invention relates to a cobalt-catalyzed process for manufacturing 1,3-propanediol in high yields without the use of a phosphine ligand for the cobalt catalyst.

1,3-propanediol (PDO) is an intermediate in the production of polyesters for fibers and films. It is known to prepare PDO in a two-step process involving (1) the cobalt-catalyzed hydroformylation (reaction with synthesis gas, $H_2/CO$) of ethylene oxide to intermediate 3-hydroxypropanal (HPA) and (2) subsequent hydrogenation of the HPA to PDO. The initial hydroformylation process can be carried out at temperatures greater than 100° C. and at high syngas pressures to achieve practical reaction rates. The resulting product mixture is, however, rather unselective for HPA.

In an alternate synthesis method, the cobalt catalyst is used in combination with a phosphine ligand to prepare HPA with greater selectivity and at lower temperature and pressure. However, the use of a phosphine ligand adds to the cost of the catalyst and increases the complexity of catalyst recycle.

It would be desirable to prepare HPA in a low temperature, selective process which did not require the use of a phosphine ligand with the cobalt catalyst.

It is therefore an object of the invention to provide an economical process for the preparation of 1,3-propanediol which does not require the use of a phosphine-ligated catalyst for preparation of the HPA intermediate. It is a further object of one embodiment of the invention to provide a process for the preparation of 1,3-propanediol in which essentially all the cobalt hydroformylation catalyst can be conveniently recycled.

SUMMARY OF THE INVENTION

According to the invention, 1,3-propanediol is prepared in a process comprising the steps of:

(a) contacting ethylene oxide with carbon monoxide and hydrogen in an essentially non-water-miscible solvent in the presence of an effective amount of a non-phosphine-ligated cobalt catalyst and an effective amount of a lipophilic dihydroxyarene promoter at a temperature within the range of about 50 to about 100° C. and a pressure within the range of about 500 to about 5000 psig, under reaction conditions effective to produce an intermediate product mixture comprising less than about 15 wt % 3-hydroxypropanal;

(b) adding an aqueous liquid to said intermediate product mixture and extracting into said aqueous liquid at a temperature less than about 100° C. a major portion of the 3-hydroxypropanal so as to provide an aqueous phase comprising 3-hydroxypropanal in greater concentration than the concentration of 3-hydroxypropanal in said intermediate product mixture, and an organic phase comprising at least a portion of the cobalt catalyst or a cobalt-containing derivative thereof and at least a portion of the lipophilic dihydroxyarene;

(c) separating the aqueous phase from the organic phase;

(d) contacting the aqueous phase comprising 3-hydroxypropanal with hydrogen in the presence of a hydrogenation catalyst at a pressure of at least about 100 psig and a temperature during at least a portion of the hydrogenation step of at least 40° C. to provide a hydrogenation product mixture comprising 1,3-propanediol;

(e) recovering 1,3-propanediol from said hydrogenation product mixture; and (f) returning at least a portion of the organic phase comprising cobalt catalyst and lipophilic dihydroxyarene to the process of step (a).

The process enables the production of 1,3-propanediol in high yields and selectivity without the use of a phosphine ligated cobalt catalyst in the hydroformylation step. The process also enables the recovery and recycle of essentially all the cobalt catalyst.

DETAILED DESCRIPTION OF THE INVENTION

Figure 1:
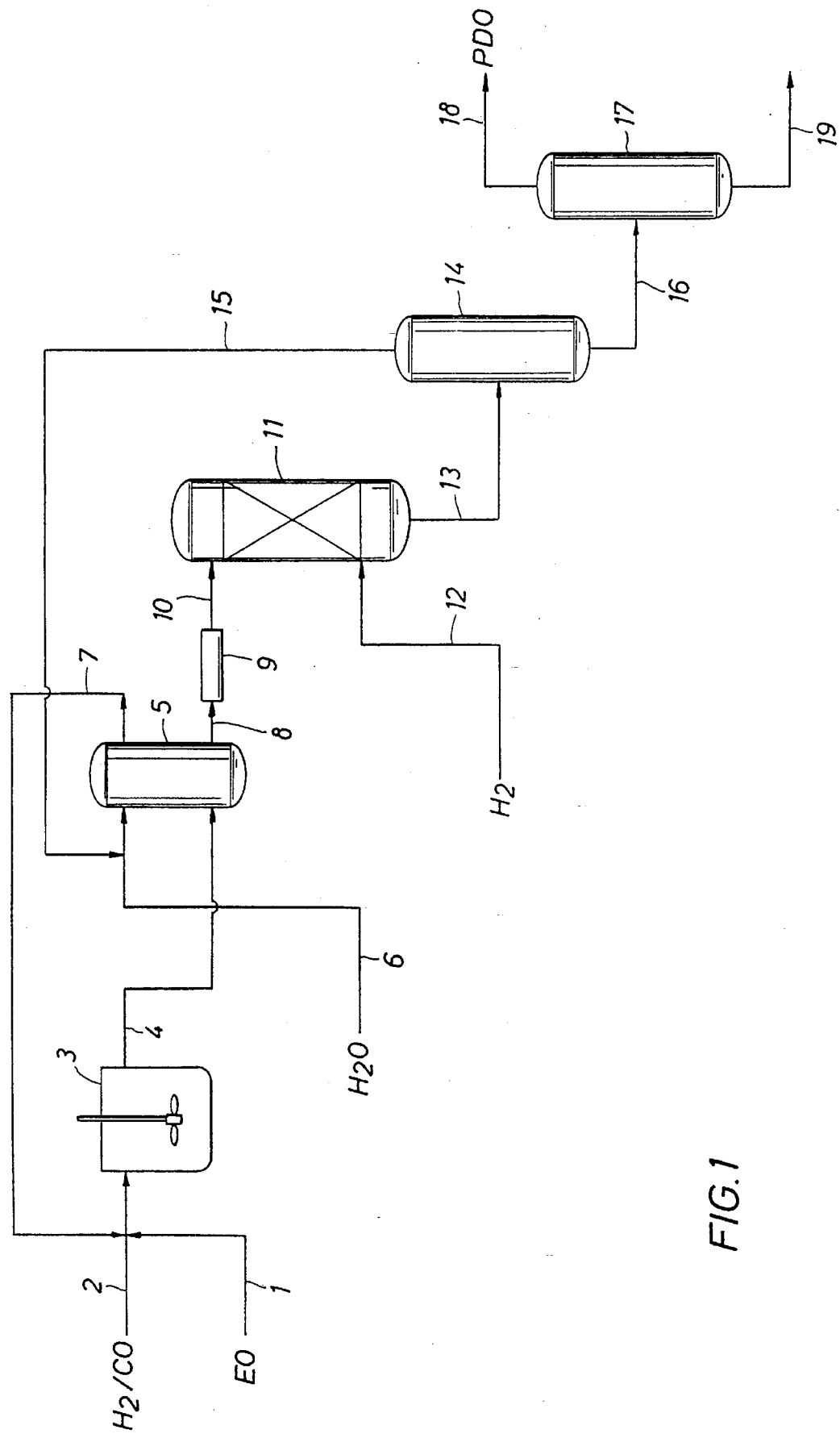
FIG. 1 is a schematic flow diagram of one embodiment of the invention 1,3-propanediol preparation process.

The invention 1,3-propanediol preparation process can be conveniently described by reference to FIG. 1. Separate or combined streams of ethylene oxide 1, carbon monoxide and hydrogen 2 are charged to hydroformylation vessel 3, which can be a pressure reaction vessel such as a bubble column or agitated tank, operated batchwise or in a continuous manner. The feed streams are contacted in the presence of a non-phosphine-ligated cobalt catalyst, i.e., a cobalt carbonyl composition which has not been prereacted with a phosphine ligand. The hydrogen and carbon monoxide will generally be introduced into the reaction vessel in a molar ratio within the range of about 1:2 to about 8:1, preferably about 1.5:1 to about 5:1.

The reaction is carried out under conditions effective to produce a hydroformylation reaction product mixture containing a major portion of 3-hydroxypropanal (HPA) and a minor portion of acetaldehyde, while maintaining the level of 3-hydroxypropanal in the reaction mixture at less than 15 wt %, preferably within the range of about 5 to about 10 wt %. (To provide for solvents having different densities, the desired concentration of HPA in the reaction mixture can be expressed in molarity, i.e., less than 1.5M, preferably within the range of about 0.5 to about 1M.) Generally, the hydroformylation reaction is carried out at elevated temperature less than 100° C., preferably about 60° to about 90° C., most preferably about 75° to about 85° C., and at a pressure within the range of about 500 to about 5000 psig, preferably (for process economics) about 1000 to about 3500 psig, with higher pressures generally imparting greater selectivity. The concentration of 3-hydroxypropanal in the intermediate product mixture can be controlled by regulation of process conditions such as ethylene oxide concentration, catalyst concentration, reaction temperature and residence time. In general, relatively low reaction temperatures (below about 90° C.) and relatively short residence times (about 20 minutes to about 1 hour) are preferred. In the practice of the invention it is possible to achieve HPA yields (based on ethylene oxide conversion of greater than 80%, with formation of more than 7 wt % HPA in the dilute hydroformylation product mixture, at rates greater than 30 $h^{-1}$. (Catalytic rates are referred to herein in terms of "turnover frequency" or "TOF" and are expressed in units of moles per mole of cobalt per hour, or $h^{-1}$.) Reported rates are based on the observation that, before a majority of the ethylene oxide is converted, the reaction is essentially zero-order in ethylene oxide concentration and proportional to cobalt concentration.

The hydroformylation reaction is carried out in a liquid solvent inert to the reactants. By "inert" is meant that the solvent is not consumed during the course of the reaction. In general, ideal solvents for the phosphine ligand-free process will solubilize carbon monoxide, will be essentially non-water-miscible and will exhibit low to moderate polarity such that the 3-hydroxypropanal intermediate will be solubilized to the desired concentration of at least about 5 wt % under hydroformylation conditions, while significant solvent will remain as a separate phase upon water extraction. By "essentially non-water-miscible" is meant that the solvent has a solubility in water at 25° C. of less than 25 wt % so as to form a separate hydrocarbon-rich phase upon water extraction of HPA from the hydroformylation reaction mixture. Preferably this solubility is less than about 10%, most preferably less than about 5 wt %. The solubilization of carbon monoxide in the selected solvent will generally be greater than 0.15 v/v (1 atm, 25° C.), preferably greater than 0.25 v/v, expressed in terms of Ostwald coefficients.

The preferred class of solvents are alcohols and ethers which can be described according to the formula

in which $R_1$ is hydrogen or $C_{1-20}$ linear, branched, cyclic or aromatic hydrocarbyl and $R_2$ is a $C_{1-20}$ linear, branched, cyclic or aromatic $C_{1-20}$ hydrocarbyl, alkoxy, or mono- or polyalkylene oxide. The most preferred hydroformylation solvents can be described by the formula

in which $R_1$ is hydrogen or $C_{1-8}$ hydrocarbyl and $R_3$, $R_4$ and $R_5$ are independently selected from $C_{1-8}$ hydrocarbyl, alkoxy and alkylene oxide. Such ethers include, for example, methyl-t-butyl ether, ethyl-t-butyl ether, ethoxyethyl ether, phenylisobutyl ether, diphenyl ether, diethyl ether, and diisopropyl ether. Blends of solvents such as tetrahydrofuran/toluene, tetrahydrofuran/heptane and t-butylalcohol/hexane can also be used to achieve the desired solvent properties. The currently preferred solvent, because of the high yields of HPA which can be achieved under moderate reaction conditions, is methyl-t-butyl ether.

The catalyst is a non-phosphine-ligated cobalt carbonyl compound. Although phosphine-ligated catalysts are active for hydroformylation reactions, the invention process is designed to achieve good yield and selectivity without the additional expense of the ligand. The cobalt catalyst can be supplied to the hydroformylation reactor in essentially any form including metal, supported metal, Raney-cobalt, hydroxide, oxide, carbonate, sulfate, acetylacetonate, salt of a carboxylic acid, or as an aqueous cobalt salt solution, for example. It may be supplied directly as a cobalt carbonyl such as dicobaltoctacarbonyl or cobalt hydridocarbonyl. If not supplied in the latter forms, operating conditions can be adjusted such that cobalt carbonyls are formed in situ via reaction with $H_2$ and CO, as described in J. Falbe, "Carbon Monoxide in Organic Synthesis," Springer-Verlag, N.Y. (1970) In general, catalyst formation conditions will include a temperature of at least 50° C. and a carbon monoxide partial pressure of at least about 100 psig. For more rapid reaction, temperatures of about 120° to 200° C. should be employed, at CO pressures of at least 500 psig. Addition of high surface area activated carbons or zeolites, especially those containing or supporting platinum or palladium metal, can accelerate cobalt carbonyl formation from noncarbonyl precursors. The resulting catalyst is maintained under a stabilizing atmosphere of carbon monoxide, which also provides protection against exposure to oxygen. The most economical and preferred catalyst activation and reactivation (of recycled catalyst) method involves preforming the cobalt salt (or derivative) under $H_2/CO$ in the presence of the catalyst promoter employed for hydroformylation. The conversion of $Co^{+2}$ to the desired cobalt carbonyl is carried out at a temperature within the range of about 75 to about 200° C, preferably about 100° to about 140° C. and a pressure within the range of about 1000 to about 5000 psig for a time preferably less than about 3 hours. The preforming step can be carried out in a pressurized preforming reactor or in situ in the hydroformylation reactor.

The amount of cobalt present in the reaction mixture will vary depending upon the other reaction conditions, but will generally fall within the range of about 0.01 to about 1 wt %, preferably about 0.05 to about 0.3 wt %, based on the weight of the reaction mixture.

The hydroformylation reaction mixture will include a lipophilic dihydroxyarene to accelerate the reaction rate without imparting hydrophilicity (water solubility) to the active catalyst. By "lipophilic" is meant that the promoter tends to remain in the organic phase after extraction of HPA with water. The dihydroxyarene will be present in an amount effective to promote the hydroformylation reaction to HPA, generally an amount within the range of about 0.01 to about 0.6 moles per mole of cobalt.

Suitable dihydroxyarenes include those represented by formula (1):

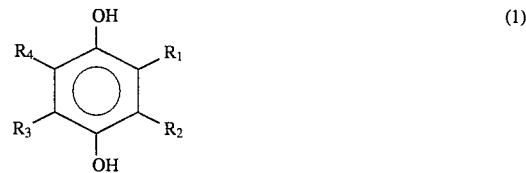

in which two hydroxyl groups are positioned on the same ring, each R group is independently selected from halide, $C_{1-25}$ linear, branched, cyclic or aromatic hydrocarbyl, alkoxy and mono- and polyalkylene oxide. Two or more R groups together may form a cyclic or aromatic ring. Examples include hydroquinone, catechol, dihydroxynaphthalenes and dihydroxyanthralenes.

It is generally preferred to regulate the concentration of water in the hydroformylation reaction mixture, as excessive amounts of water reduce (HPA+PDO) selectivity below acceptable levels and may induce formation of a second liquid phase. At low concentrations, water can assist in promoting the formation of the desired cobalt carbonyl catalyst species. Acceptable water levels will depend upon the solvent used, with more polar solvents generally being more tolerant of higher water concentrations. For example, optimum water levels for hydroformylation in methyl-t-butyl ether solvent are believed to be within the range of about 1 to about 2.5 wt %.

Following the hydroformylation reaction, hydroformylation reaction product mixture 4 containing 3-hydroxypropanal, the reaction solvent, 1,3-propanediol, the cobalt catalyst and a minor amount of reaction by-products, is cooled and passed to extraction vessel 5, wherein an aqueous liquid, generally water and optional miscibilizing solvent, are added via 6 for extraction and concentration of the HPA for the subsequent hydrogenation step. Liquid extraction can be effected by any suitable means, such as mixer-settlers, packed or trayed extraction columns, or rotating disk contactors. Extraction can if desired be carried out in multiple stages. The water-containing hydroformylation reaction product mixture can optionally be passed to a settling tank (not shown) for resolution of the mixture into aqueous and organic phases. The amount of water added to the hydroformylation reaction product mixture will generally be such as to provide a water:mixture ratio within the range of about 1:1 to about 1:20, preferably about 1:5 to about 1:15. The addition of water at this stage of the reaction may have the additional advantage of suppressing formation of undesirable heavy ends. Extraction with a relatively small amount of water provides an aqueous phase which is greater than 20 wt % HPA, preferably greater than 35 wt % HPA, permitting economical hydrogenation of the HPA to PDO. The water extraction is preferably carried out at a temperature within the range of about 25° to about 55° C., with higher temperatures avoided to minimize condensation products (heavy ends) and catalyst disproportionation to inactive, water-soluble cobalt species. In order to maximize catalyst recovery, it is preferred to perform the water extraction under 50–200 psig carbon monoxide at 25° to 55° C.

The organic phase containing the reaction solvent and the major portion of the cobalt catalyst can be recycled from the extraction vessel to the hydroformylation reaction via 7. Aqueous extract 8 is optionally passed through one or more acid ion exchange resin beds 9 for removal of any cobalt catalyst present, and the decobalted aqueous product mixture 10 is passed to hydrogenation vessel 11 and reacted with hydrogen 12 in the presence of a hydrogenation catalyst to produce a hydrogenation product mixture 13 containing 1,3-propanediol. The hydrogenation step may also revert some heavy ends to PDO. The solvent and extractant water 15 can be recovered by distillation in column 14 and recycled to the water extraction process via a further distillation (not shown) for separation and purge of light ends. PDO-containing stream 16 can be passed to distillation column 17 for recovery of PDO 18 from heavy ends 19.

Hydrogenation of the HPA to PDO can be carried out in aqueous solution at an elevated temperature during at least a portion of the hydrogenation step of about 40° C., generally within the range of about 50° to about 175° C., under a hydrogen pressure of at least about 100 psig, generally within the range of about 200 to about 2000 psig. The reaction is carried out in the presence of a hydrogenation catalyst such as any of those based upon Group VIII metals, including nickel, cobalt, ruthenium, platinum and palladium, as well as copper, zinc and chromium and mixtures and alloys thereof. Nickel catalysts, including bulk, supported and fixed-bed forms, provide acceptable activities and selectivities at moderate cost. Highest yields are achieved under slightly acidic reaction conditions.

Commercial operation will require efficient cobalt catalyst recovery with essentially complete recycle of cobalt to the hydroformylation reaction. The preferred catalyst recovery process involves two steps, beginning with the above-described water extraction of HPA from the hydroformylation product mixture. A majority of the cobalt catalyst will remain in the organic phase, with the remaining cobalt catalyst passing into the water phase. The organic phase can be recycled to the hydroformylation reactor, with optional purge of heavy ends. Optionally, further decobalting of catalyst in the water layer can be effected by suitable method, such as complete or partial oxidation of cobalt followed by precipitation and filtration, distillation, deposition on a solid support, or extraction using a suitable extractant, preferably prior to final cobalt removal by ion exchange (9).

The invention process permits the selective and economic synthesis of PDO at moderate temperatures and pressures without the use of a phosphine ligand for the hydroformylation catalyst. The process involves preparation of a reaction product mixture dilute in intermediate HPA, then concentration this HPA by water extraction followed by hydrogenation of the aqueous HPA to PDO.

EXAMPLE 1

A 300-ml stirred batch reactor was charged under nitrogen with 0.87 g dicobaltoctacarbonyl, 1.5 g toluene (marker), 2 g deionized water and 146 g methyl-t-butyl ether (MTBE). The nitrogen atmosphere was flushed with $H_2$, and the reactor was filled to 600 psig $H_2$ and then to 1200 psig with 1:1 $CO/H_2$. Reactor contents were heated to 80° C. for one hour, and 10 g of ethylene oxide was then injected, with simultaneous increase in reactor pressure to 1500 psig via addition of 1:1 $CO/H_2$. Reactor contents were sampled and analyzed via capillary g.c. (with flame ionization detector) at approximately 40% and nearly 100% conversion of EO, which occurred within two hours. At approximately 40% conversion, 3.3 wt % HPA had been formed at a rate of 18 $h^{-1}$.

EXAMPLE 2

Example 1 was repeated in the absence of added water and with addition of 0.14 g of sodium acetate trihydrate as promoter, added at a ratio Na/Co of 0.2. HPA was formed at a rate of 41 $h^{-1}$. After cooling and addition of 30 g deionized water for extraction, only 77% of the cobalt catalyst remained with the upper solvent layer. 23% of the cobalt was extracted with the aqueous product. This fraction corresponds approximately to the amount of sodium acetate added to promote the reaction.

EXAMPLE 3

These experiments illustrate the effectiveness of hydroquinone both to accelerate the hydroformylation reaction and to permit the recycle of essentially all the cobalt catalyst in the organic phase following water extraction of product HPA. Example 1 was repeated with addition of 0.14 g of hydroquinone as promoter, for a ratio of 0.25 moles promoter per mole of cobalt. At approximately 50% conversion, 4.7 wt % HPA had been formed at a rate of 25.9 $h^{-1}$, or a 44% rate increase over that observed in the absence of promoter in Example 1. The reaction was terminated at 98% conversion of ethylene oxide, with formation of 9.4 wt % HPA.

Following the reaction, the mixture was cooled to room temperature. 31.6 g of deionized water were added for extraction of product under 200 psig synthesis gas. After 30 minutes, mixing was terminated and 38.32 g of an aqueous product layer containing 18 wt % HPA was isolated. The aqueous layer contained 115 ppm cobalt, or only 4% of the total charged. The upper organic layer (99.8 g) was analyzed to contain 0.19 wt % cobalt. Recycle of 96% of the cobalt catalyst with the organic layer represents reduction in cobalt loss by a factor of 6, relative to that observed with sodium acetate promotion in Example 2.

We claim:

1. A process for preparing 1,3-propanediol comprising the steps of:
   (a) contacting, at a temperature within the range of about 50° to about 100° C. and a pressure within the range of about 500 to about 5000 psig, ethylene oxide with carbon monoxide and hydrogen in an essentially non-water miscible solvent in the presence of an effective amount of a non-phosphine-ligated cobalt catalyst and an effective amount of a lipophilic dihydroxyarene promoter under reaction conditions effective to produce an intermediate product mixture comprising less than 15 wt % 3-hydroxypropanal;
   (b) adding an aqueous liquid to said intermediate product mixture and extracting into said aqueous liquid a major portion of the 3-hydroxypropanal at a temperature less than about 100° to provide an aqueous phase comprising 3-hydroxypropanal in greater concentration than the concentration of 3-hydroxypropanal in the intermediate product mixture, and an organic phase comprising at least a portion of the cobalt catalyst or a cobalt-containing derivative thereof and at least a portion of the lipophilic dihydroxyarene;
   (c) separating the aqueous phase from the organic phase;
   (d) contacting the aqueous phase comprising 3-hydroxypropanal with hydrogen in the presence of a hydrogenation catalyst at a temperature during at least a portion of the hydrogenation step of at least about 40° C. to provide a hydrogenation product mixture comprising 1,3-propanediol;
   (e) recovering 1,3-propanediol from the hydrogenation product mixture; and
   (f) returning at least a portion of the organic phase comprising cobalt compound and lipophilic dihydroxyarene to the process of step (a).

2. The process of claim 1 in which the 3-hydroxypropanal in the intermediate product mixture is produced at a level within the range of about 5 to about 10 wt %.

3. The process of claim 1 in which step (a) is carried out at a temperature within the range of about 60° to about 90° C.

4. The process of claim 1 in which the lipophilic dihydroxyarene is selected from hydroquinone and catechol.

5. The process of claim 1 in which the lipophilic hydroquinone is hydroquinone.

6. The process of claim 3 in which the solvent of step (a) comprises an ether.

7. The process of claim 6 in which the dihydroxyarene is selected from the group consisting of hydroquinone and methyl-, ethyl-, methoxy- and ethoxy-substituted hydroquinones.

8. The process of claim 3 in which step (a) is carried out at a pressure within the range of about 1000 to about 3500 psig.

9. The process of claim 1 in which the solvent of step (a) comprises methyl-t-butyl ether.

10. The process of claim 9 in which step (a) is carried out at a temperature within the range of about 75° to about 85° C.

11. The process of claim 1 which further comprises carrying out step (b) under carbon monoxide.

12. The process of claim 11 in which the promoter is present in an amount within the range of about 0.01 to about 0.6 moles per mole of cobalt.

13. The process of claim 1 in which step (c) further comprises removing at least a portion of any cobalt compound present in the aqueous phase.

14. The process of claim 1 in which the $H_2/CO$ ratio of step (a) is within the range of about 1.5:1 to about 5:1.

15. The process of claim 1 in which step (a) is carried out at a rate expressed as turnover frequency greater than about 30 $h^{-1}$.

16. A process for preparing 1,3-propanediol comprising the steps of:
   (a) reacting, at a temperature within the range of about 60° to about 90° C. and a pressure within the range of about 1000 to about 3500 psig, ethylene oxide, carbon monoxide and hydrogen in an essentially non-water-miscible solvent comprising methyl-t-butyl ether in the presence of a catalytic amount of a non-phosphine-ligated cobalt catalyst and about 0.01 to about 0.6 wt % of hydroquinone, under reaction conditions effective to produce an intermediate product mixture comprising 3-hydroxypropanal in a concentration within the range of about 5 to about 10 wt %;
   (b) adding water to said intermediate product mixture in an amount within the range of about 10 to about 25 weight percent based on the weight of the intermediate product mixture and permitting the water-containing intermediate product mixture to resolve into an aqueous phase comprising 3-hydroxypropanal in a concentration of at least about 20 wt % and an organic phase comprising a major portion of the cobalt catalyst or a cobalt-containing derivative thereof and at least a portion of the hydroquinone;
   (c) separating the aqueous phase from the organic phase and subsequently removing any cobalt catalyst from the aqueous phase;
   (d) contacting the aqueous phase comprising 3-hydroxypropanal with hydrogen in the presence of a hydrogenation catalyst at a pressure of at least about 100 psig and a temperature of at least about 40° C. to provide a hydrogenation product mixture comprising 1,3-propanediol;
   (e) recovering 1,3-propanediol from the hydrogenation product mixture; and
   (f) returning at least a portion of the organic phase comprising cobalt compound and hydroquinone to the process of step (a).

* * * * *